United States Patent [19]
Luber

[11] Patent Number: 5,807,580
[45] Date of Patent: Sep. 15, 1998

[54] FILM COATED TABLET COMPOSITIONS HAVING ENHANCED DISINTEGRATION CHARACTERISTICS

[75] Inventor: Joseph R. Luber, Quakertown, Pa.

[73] Assignee: McNeil-PPC, Inc., Skillman, N.J.

[21] Appl. No.: 739,849

[22] Filed: Oct. 30, 1996

[51] Int. Cl.⁶ .............................. A61K 9/36; A61K 9/32; A61K 47/38
[52] U.S. Cl. .................. 424/480; 427/2.21; 514/819; 424/717; 424/687; 424/716; 424/686
[58] Field of Search ..................... 424/480, 466, 424/474–482; 427/2.21; 514/819

[56] References Cited

U.S. PATENT DOCUMENTS

| | | | |
|---|---|---|---|
| 4,556,552 | 12/1985 | Porter et al. | 424/482 |
| 4,629,620 | 12/1986 | Lindahl et al. | 424/482 |
| 4,965,072 | 10/1990 | Alexander et al. . | |
| 5,098,715 | 3/1992 | McCabe et al. . | |
| 5,122,385 | 6/1992 | Daher et al. . | |
| 5,178,868 | 1/1993 | Malmqvist-Granlund et al. | 424/482 |
| 5,472,712 | 12/1995 | Oshlack et al. . | |
| 5,505,962 | 4/1996 | Sparks . | |

FOREIGN PATENT DOCUMENTS 0 670 160 A1  10/1994  European Pat. Off. .

*Primary Examiner*—Edward J. Webman
*Attorney, Agent, or Firm*—Kenneth J. Dow

[57] ABSTRACT

A pharmaceutical composition for oral administration comprising a film coated tablet exhibiting enhanced disintegration characteristics, said film coating comprising a hydrophilic film forming polymer such as hydroxypropyl methylcellulose and an alkaline agent wherein the alkaline agent reduces the disintegration time of the film coating by increasing the rate of removal of the film coating polymers.

7 Claims, No Drawings

FILM COATED TABLET COMPOSITIONS HAVING ENHANCED DISINTEGRATION CHARACTERISTICS

FIELD OF THE INVENTION

The present invention relates to pharmaceutical compositions and more particularly film coated tablet compositions having enhanced disintegration characteristics.

BACKGROUND OF THE INVENTION

Standard therapy in the treatment of many illnesses is the administration of a medicament in a tablet dosage form, which requires the patient to swallow the tablet intact. In order to improve on the ability of a patient to swallow a tablet, it is known in the art to coat the surface of the tablet with a polymeric film. This film has several benefits for the patient. First, it reduces the adhesion of the tablet to the inner surface of the mouth, thereby increasing the patient's ability to swallow the tablet. Second, the film aids in masking the unpleasant taste for certain drugs. In addition, the film coating can protect components from atmospheric degradation and improve appearance.

Polymeric films typically used in such film coating include (1) vinyl polymers such as polyvinylpyrrolidone, polyvinyl alcohol and acetate, (2) cellulosics such as methyl and ethyl cellulose, hydroxyethyl cellulose and hydroxypropyl methylcellulose, (3) acrylates and methacrylates, (4) copolymers such as the vinyl-maleic acid and styrene-maleic acid types, and (4) natural gums and resins such as zein, gelatin, shellac and acacia. See Remington's Pharmaceutical Sciences, 15th Ed. Mack Publishers (1975) p. 1613.

While the film coating adds certain advantages to the tablet formulations, one disadvantage is that the coating may reduce the onset of action of the drug by retarding disintegration of the tablet. This can effect the performance of certain medications where a fast onset of action is desirable, for example, antacids. Thus there is a need for a film coating composition which exhibits enhanced disintegration characteristics thereby providing more rapid delivery of the medicament and a faster onset of action.

The use of disintegrating agents such as dried starch, sodium alginate, lactose, sodium bicarbonate, calcium carbonate, polyvinyl pyrrolidone, microcrystalline cellulose and the like in the tablet core or granulation mixture of a swallowable tablet formulation is well known. For example, U.S. Pat. No. 4,965,072 discloses the use of a mixture of magnesium sulphate heptahydrate and sodium hexametaphosphate to prepare a granulating composition with an active ingredient, which, when formulated into a swallowable tablet, exhibits rapid disintegration or dispersion. However, the use of disintegrating agents in the tablet core in such a manner does not address the problem associated with the slow dissolution of the polymeric film in a film coated tablet.

SUMMARY OF THE INVENTION

A pharmaceutical composition for oral administration comprising a film coated tablet exhibiting enhanced disintegration characteristics, said film coating comprising a hydrophilic film forming polymer and an alkaline agent wherein the alkaline agent reduces the disintegration time of the film coating by increasing the rate of removal of the film coating polymers. When the coated tablet contacts the gastric acid, it immediately reacts with the alkaline agent in the film coating, and numerous holes are produced in the film coat. The gastric fluid is then able to rapidly penetrate the coating, and begin disintegration of the tablet core. Preferably, the alkaline agent is selected from an alkali metal or alkali earth metal carbonate or bicarbonate such as sodium or potassium bicarbonate.

DETAILED DESCRIPTION

In accordance with the present invention, the film coating is formed on at least a portion, preferably on all, of the exposed surface of the core containing the pharmaceutical actives. The film forming agent is typically a water soluble film forming polymer, such as hydroxypropyl methylcellulose, methylcellulose, ethylcellulose, hydroxypropyl cellulose, povidone, polydextrose, lactose, maltodextrin, acrylic polymer, and mixtures thereof. The film coating may optionally contain a plasticizer, such as castor oil, polyethylene glycol, propylene glycol or glycerine, and a coloring or pacifying agent. The film coating may also contain a flavoring and/or sweetening agent to improve palatability. A preferred blend of hydroxypropyl methylcellulose, a plasticizer and a colorant is commercially available from Colorcon, West Point, Pa. under the tradename OPADRY®. OPADRY Red is a red powder which is dispersed in water to form an aqueous film coating. This product contains hydroxypropyl methylcellulose, FD&C red no. 40 aluminum lake, polyethylene glycol, titanium dioxide, FD&C yellow no. 6 aluminum lake and polysorbate 80.

The alkaline agent may be selected from any pharmaceutically acceptable alkaline agent which is capable of reducing the disintegration time of the film coating by increasing the rate of removal of the film coating polymers. Preferably, the alkaline agent is selected from an alkali metal or alkali earth metal carbonate or bicarbonate such as sodium or potassium bicarbonate.

The dispersion will generally contain (w/w) about 5 to about 20 percent of the film forming polymer, about 1 to about 7 percent of the alkaline agent, and about 73 to about 94 percent purified water. A preferred aqueous film coating formulation is composed of about 8 to 10% by weight hydroxypropyl methylcellulose, about 0.1 to 0.2% by weight castor oil, and about 1.5 to 3.5% by weight potassium bicarbonate dissolved in water to produce an aqueous solution. Obviously equivalents for these compounds as are well known in the tablet coating art, may be used in approximately the same proportions.

The film coating is applied to the cores as an aqueous dispersion and dried to form a thin film coating. The film coating dispersion is manufactured by hydrating the water soluble film-forming polymer and diluting to the suitable viscosity for coating the tablet cores. The required quantity of the alkaline agent is dissolved in the water used to hydrate and dilute the polymeric material.

The dispersion is applied to standard tablet or caplet cores containing the medicament. The cores are prepared in accordance with standard pharmaceutical tableting techniques, including wet-granulation, dry-granulation, direct compression, spheronization and the like. The dispersion is applied to the cores using conventional pharmaceutical coating equipment, such as an Accela-Cota® coating pan from Thomas Engineering, Inc., Hoffman Estates, Ill. Other film coating techniques suitable for use in the present invention are described in *Remington's Pharmaceutical Sciences* (edited by A. L. Gennaro), Mack Publishing Co., Easton, Pa., 18th ed., Chapter 90 (1990), which is hereby incorporated by reference. The preferred method for applying the film coatings of the present invention is spray coating using conventional coating equipment but fluid-bed coating may also be employed.

The film coating (dried) generally constitutes from about 1 to about 10, preferably about 2 to about 6, percent by weight of the total weight of the solid dosage form.

The film coatings of the present invention may be employed for the coating of a variety of medicaments where a quick onset of action is desirable. The preferred pharmaceutical tablets with which the film coatings of the present invention is used contains an antacid where an immediate release of the active ingredient in the stomach is desirable to neutralize stomach acid and provide immediate relief from acid indigestion, heartburn and the like. Typical antacids are made from a variety of inorganic salts such as calcium carbonate, sodium bicarbonate, magnesium salts and aluminum salts. Magnesium hydroxide and aluminum hydroxide are the most potent magnesium and aluminum salts and are often used in combination. In addition, magnesium oxide, magnesium carbonate, aluminum phosphate, magaldrate, magnesium trisilicate, and aluminum sucrose sulfate (sucralfate) may also be employed with the present invention. In a preferred embodiment, the antacid is selected from a combination of calcium carbonate and magnesium carbonate or calcium carbonate and magnesium hydroxide. The amount of antacid in the preparation may conveniently be, for example, in the range of 10%–90% w/v of the composition. Advantageously, an H2 receptor blocking agent such as famotidine, ranitidine and cimetidine may also be combined with the antacid, or the film coating can be applied to the H2 receptor blocking dose. Other active ingredients for which the coatings of the present invention are suitable include antiflatulents, anti-inflammatory agents, analgesics, anti-diarrheals and combinations thereof.

When the film-coated tablets or caplets of the present invention are administered to a patient, the tablet or caplet contacts the gastric acid of the stomach, which immediately reacts with the alkaline agent in the film coating, and numerous holes are produced in the film coat. The gastric fluid is then able to rapidly penetrate the coating, and begin disintegration of the tablet core. Thus, the tablets or caplets prepared in accordance with the present invention exhibit enhanced disintegration characteristics in gastric acid when compared to conventional film-coated tablets or caplets.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLE 1

Calcium Carbonate/Magnesium Carbonate Film Coated Antacids

Five film coating dispersion formulations were prepared, each containing different levels of potassium bicarbonate alkaline agent and used to coat calcium carbonate-magnesium carbonate caplet cores. The ingredient amounts for the film coating dispersions for each caplet were as follows:

| Ingredient | mg/tab |
| --- | --- |
| Hydroxypropyl Methylcellulose | 27.88 |
| Castor Oil | 0.12 |
| Example A. Potassium Bicarbonate | 0.0 |
| Example B. Potassium Bicarbonate | 2.8 |
| Example C. Potassium Bicarbonate | 7.0 |
| Example D. Potassium Bicarbonate | 9.8 |
| Example E. Potassium Bicarbonate | 18.7 |

Purified Water q.s. amount to make 9% aqueous solution of the polymer.

The film coating dispersions are prepared by filling the required amount of Purified Water into a mixing vessel, adding the required amount of Castor Oil plasticizer and mixing for about 5 minutes. The required amount of Potassium Bicarbonate is added to the mixing vessel and is mixed for an additional 5 minutes. The required amount of hydroxypropyl methylcellulose is then slowly fed into the mixing vessel and the mixer speed is increased as necessary and mixed until all the polymer is dissolved. Mixing is then terminated and the mixture is allowed to deaerate for about 2 hours.

The dispersion is then used to coat compressed core caplets having the following composition:

| Ingredient | mg/caplet |
| --- | --- |
| Calcium Carbonate | 335.0 |
| Magnesium Carbonate | 295.0 |
| Microcrystalline Cellulose | 64.0 |
| Croscarmellose Sodium | 30.0 |
| Magnesium Stearate | 4.0 |
| Total | 728.0 |

Coating was performed in a VECTOR Coating Pan using standard coating procedures.

The disintegration times of the five film coated core samples were evaluated using the following procedure:

A. Put 250 ml of N/10 HCL into a 400 ml beaker, and heat to 37° C. (no stirring);

B. Individually suspend three tablets from wires in the solution from "A" and start timer;

C. Record time when tablet breaks in half. The results are shown in Table 1.

TABLE 1

| Sample | Average DT in min. |
| --- | --- |
| Example A | 5 |
| Example B | 4.25 |
| Example C | 1.8 |
| Example D | 1.6 |
| Example E | 1.5 |

DT = disintegration time.

The results set forth in Table 1 demonstrate that the disintegration time of the tablets having the coatings of the present invention are markedly reduced when compared to the film coated tablets which do not contain the alkaline agent in accordance with the present invention.

EXAMPLE 2

Famotidine/Calcium Carbonate/Magnesium Hydroxide Film Coated Tablets

A film coating dispersion in accordance with the present invention is prepared and used to coat famotidine/calcium carbonate/magnesium hydroxide caplet cores. The ingredient amounts for the film coating dispersions for each caplet are as follows:

| Ingredient | mg/tab |
|---|---|
| Hydroxypropyl Methylcellulose | 10.00 |
| Propylene Glycol | 0.30 |
| Sodium Carbonate | 7.00 |
| Maltodextrin | 5.00 |
| Purified Water | q.s. amount to make 7% aqueous solution of the hydroxypropyl methylcellulose polymer. |

The film coating dispersion is prepared by filling the required amount of Purified Water into a mixing vessel, adding the required amount of propylene glycol plasticizer and mixing for about 5 minutes. The required amount of sodium carbonate is added to the mixing vessel and is mixed for an additional 5 minutes. The required amount of hydroxypropyl methylcellulose and maltodextrin is then slowly fed into the mixing vessel and the mixer speed is increased as necessary and mixed until all the polymer is dissolved. Mixing is then terminated and the mixture is allowed to deaerate for about 2 hours.

The dispersion is then used to coat compressed core caplets having the following composition:

| Ingredient | mg/caplet |
|---|---|
| Calcium Carbonate | 400.0 |
| Magnesium Hydroxide | 100.0 |
| Famotidine | 10.0 |
| Microcrystalline Cellulose | 102.0 |
| Croscarmellose Sodium | 30.0 |
| Magnesium Stearate | 8.0 |
| Total | 650.0 |

Coating was performed in a ACELLA COTA Coating Pan using standard coating procedures. The finished famotidine/calcium carbonate/magnesium hydroxide caplets are useful for the treatment of gastric conditions such as heartburn, acid indigestion and peptic ulcer disease.

EXAMPLE 3

Acetaminophen Film Coated Tablets

A film coating dispersion in accordance with the present invention is prepared and used to coat acetaminophen caplet cores. The ingredient amounts for the film coating dispersions for each caplet are as follows:

| Ingredient | mg/tab |
|---|---|
| Hydroxypropyl cellulose | 10.00 |
| Glycerin | 0.20 |
| Calcium Carbonate | 10.00 |
| Purified Water | q.s. amount to make 9% aqueous solution of the hydroxypropyl cellulose polymer. |

The film coating dispersion is prepared by the method of Example 2, substituting the glycerin for the propylene glycol plasticizer and the calcium carbonate alkaline agent for the sodium carbonate. The dispersion is then used to coat compressed core caplets containing 500 mg acetaminophen in association with conventional excipients.

EXAMPLE 4

Simethicone Film Coated Tablets

A film coating dispersion in accordance with the present invention is prepared and used to coat simethicone caplet cores. The ingredient amounts for the film coating dispersions for each caplet are as follows:

| Ingredient | mg/tab |
|---|---|
| Methyl cellulose | 15.00 |
| Propylene Glycol | 0.20 |
| Potassium Bicarboante | 7.00 |
| Purified Water | q.s. amount to make 10% aqueous solution of the methyl cellulose polymer. |

The film coating dispersion is prepared by the method of Example 2, substituting the potassium bicarbonate alkaline agent for the sodium carbonate. The dispersion is then used to coat compressed core caplets containing 125 mg simethicone in association with conventional excipients.

I claim:

1. A pharmaceutical composition for oral administration comprising a film coated tablet or caplet exhibiting rapid disintegration characteristics in gastric acid, said film coating consisting essentially of a hydroxypropyl methylcellulose film forming polymer and an alkaline agent.

2. A pharmaceutical tablet or caplet according to claim 1 wherein the alkaline agent is selected from an alkali metal or alkali earth metal carbonate or bicarbonate.

3. A pharmaceutical tablet or caplet according to claim 2 wherein the alkali metal or alkali earth metal carbonate or bicarbonate is selected from sodium or potassium bicarbonate.

4. A pharmaceutical tablet or caplet according to claim 1 wherein said film coating further contains a plasticizer.

5. A pharmaceutical tablet or caplet according to claim 4, wherein the plasticizer is selected from castor oil, polyethylene glycol, propylene glycol and glycerine.

6. A pharmaceutical tablet or caplet of claim 1 wherein said film coating is a dispersion comprised of (w/w) about 5 to about 20 percent of the hydroxypropyl methylcellulose film forming polymer, about 1 to about 7 percent of the alkaline agent, and about 73 to about 94 percent purified water.

7. A method for preparing a film coated pharmaceutical tablet or caplet exhibiting rapid disintegration characteristics in gastric acid comprising the steps of:

(a) preparing an aqueous dispersion consisting essentially of a hydroxypropyl methylcellulose film forming polymer and an alkaline agent; and (b) placing an uncoated tablet or caplet in a coating pan; and (c) coating said tablet or caplet with said aqueous dispersion to form a film coated tablet or caplet.

* * * * *